(12) United States Patent
Waggoner et al.

(10) Patent No.: US 10,483,123 B2
(45) Date of Patent: Nov. 19, 2019

(54) METHOD FOR MAKING A WELL DISPOSED OVER A SENSOR

(71) Applicant: Life Technologies Corporation, Carlsbad, CA (US)

(72) Inventors: Phil Waggoner, Guilford, CT (US); Jordan Owens, Austin, TX (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/945,707

(22) Filed: Apr. 4, 2018

(65) Prior Publication Data
US 2018/0366340 A1  Dec. 20, 2018

Related U.S. Application Data (60) Provisional application No. 62/481,610, filed on Apr. 4, 2017.

(51) Int. Cl.
| | |
|---|---|
| H01L 21/311 | (2006.01) |
| G01N 27/414 | (2006.01) |
| H01L 21/02 | (2006.01) |
| H01L 21/027 | (2006.01) |
| H01L 21/285 | (2006.01) |
| H01L 21/3213 | (2006.01) |

(52) U.S. Cl.
CPC .... *H01L 21/31144* (2013.01); *G01N 27/4146* (2013.01); *G01N 27/4148* (2013.01); *H01L 21/0206* (2013.01); *H01L 21/0271* (2013.01); *H01L 21/28556* (2013.01); *H01L 21/31111* (2013.01); *H01L 21/32133* (2013.01)

(58) Field of Classification Search
CPC ........... B01L 3/502707; B01L 2200/12; B01L 2300/636; G01N 27/414–4148
See application file for complete search history.

(56) References Cited

U.S. PATENT DOCUMENTS

| | | | |
|---|---|---|---|
| 2014/0264472 A1 | 9/2014 | Fife et al. | |
| 2015/0160153 A1* | 6/2015 | Li | B01L 3/502707 257/253 |
| 2017/0059517 A1* | 3/2017 | Bustillo | H01L 29/42324 |

OTHER PUBLICATIONS

PCT/US2018/026141, International Search Report, dated Jul. 3, 2018, 1-13.

* cited by examiner

*Primary Examiner* — Daniel P Shook (57) ABSTRACT

A method for forming a well providing access to a sensor pad includes patterning a first photoresist layer over a dielectric structure disposed over the sensor pad; etching a first access into the dielectric structure and over the sensor pad, the first access having a first characteristic diameter; patterning a second photoresist layer over the dielectric structure; and etching a second access over the dielectric structure and over the sensor pad. The second access has a second characteristic diameter. The first and second accesses overlapping. A diameter ratio of the first characteristic diameter to the second characteristic diameter is not greater than 0.7. The first access exposes the sensor pad. The second access has a bottom depth less than a bottom depth of the first access.

18 Claims, 10 Drawing Sheets

METHOD FOR MAKING A WELL DISPOSED OVER A SENSOR

CROSS-REFERENCE TO RELATED APPLICATION(S)

This application claims benefit of U.S. Provisional Application No. 62/481,610, filed Apr. 4, 2017, which is incorporated herein by reference in its entirety.

FIELD OF THE DISCLOSURE

This disclosure, in general, relates to methods for making a well over a semiconductor device.

BACKGROUND

A variety of types of chemical devices have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect or determine characteristics of the chemical reaction. The threshold voltage can, for example, be measured by applying appropriate bias voltages to the source and drain, and measuring a resulting current flowing through the chemFET. In another example, the threshold voltage can be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, for example, from the protonation or deprotonation of surface charge groups caused by the ions present in the analyte solution. The change in surface potential at the sensitive area of the ISFET affects the threshold voltage of the device, which can be measured to indicate the presence or concentration of ions within the solution. Arrays of ISFETs can be used for monitoring chemical reactions, such as DNA sequencing reactions, based on the detection of ions present, generated, or used during the reactions. More generally, large arrays of chemFETs or other types of chemical devices can be employed to detect and measure static or dynamic amounts or concentrations of a variety of analytes (e.g. hydrogen ions, other ions, compounds, etc.) in a variety of processes. The processes can, for example, be biological or chemical reactions, cell or tissue cultures or monitoring neural activity, nucleic acid sequencing, etc.

An issue that arises in the operation of large scale chemical device arrays is the susceptibility of the sensor output signals to noise. Specifically, the noise affects the accuracy of the downstream signal processing used to determine the characteristics of the chemical or biological process being detected by the sensors. It is therefore desirable to provide devices including low noise chemical devices, and methods for manufacturing such devices.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an example embodiment, a device includes a dielectric structure disposed over an array of sensors. The dielectric structure defines microwells, which include a first access exposing a sensor pad of a sensor and a second access overlapping the first access and having a characteristic diameter larger than the characteristic diameter of the first access. Together, the first access and second access form the microwell. In use, the microwell can provide a fluid path from a bulk solution through to the sensor pad. In particular, reactants or reaction byproducts associated with reactions taking place within the microwell can be measured using the sensor pad surface exposed by the first access. Optionally, a conformal metal coating, such as a titanium coating, can be disposed within the first access or the second access of the microwell, extending the sensor surface to over the surface of the well. Optionally, the dielectric structure has more than one layer. For example, the dielectric structure can have a silicon oxide layer, such as a high density plasma chemical vapor deposited silicon dioxide layer. Further, the dielectric structure can have a nitride layer, such as a silicon nitride layer. In a further example, the dielectric structure can have a silicon oxide layer, such as a tetraethyl orthosilicate (TEOS) deposited silicon dioxide layer.

In an example, a sensor pad of the sensor is disposed within a dielectric structure. The dielectric structure can have a single layer, such as a high density plasma chemical vapor deposited silicon dioxide. In another example, the dielectric structure can have a multilayer structure, such as a silicon oxide layer formed around the sensor pad, a silicon nitride layer disposed over the silicon oxide layer, and a silicon oxide layer, such as a layer formed using TEOS, disposed over the silicon nitride layer. A photoresist can be patterned to define an opening, and the dielectric structure can be etched to form a first access having a characteristic diameter associated with the opening. As used herein, the characteristic diameter is the square root of four times a cross-sectional area divided by pi (i.e., sqrt(4 A/pi)). In an example, the first access can be etched partially through the dielectric structure. In another example, the first access can be etched through the dielectric structure to expose a surface of the sensor pad. The first photoresist layer can be removed and cleaned from the work piece, and a second photoresist layer can be formed and pattern to define a second opening, larger in characteristic diameter than the first opening. The dielectric structure can be etched to form a second access overlapping the first access and formed partially through the dielectric structure. The second access does not extend to expose sensor pad. Optionally, prior to forming the second photoresist layer, a bottom anti-reflective coating is formed over the dielectric structure and at least partially within the first access. The second photoresist layer and optionally the bottom anti-reflective coating (BARC) can be cleaned from the work piece. In a further example, a conformal metal layer can be formed within the first access and the second access, for example, through sputtering or deposition. A conformal metal coating can be removed from interstitial areas surrounding the second access. The first access and the second access can define a microwell.

Figure 1:
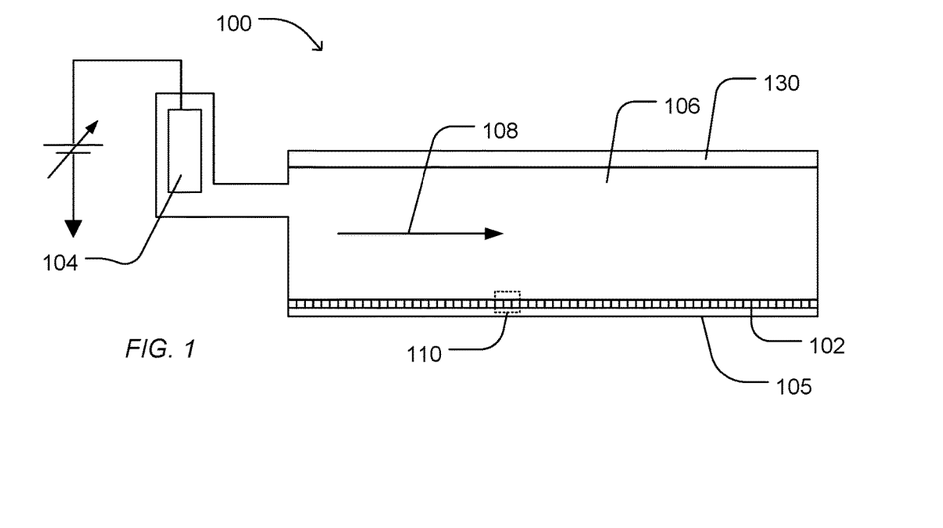
FIG. 1 includes an illustration of an exemplary system including a sensor array.

The device including the dielectric layer defining the microwell formed from the first access and second access and exposing a sensor pad finds particular use in detecting chemical reactions and byproducts, such as detecting the release of hydrogen ions in response to nucleotide incorporation, useful in genetic sequencing, among other applications. In a particular embodiment, a sequencing system includes a flow cell in which a sensory array is disposed, includes communication circuitry in electronic communication with the sensory array, and includes containers and fluid controls in fluidic communication with the flow cell. In an example, FIG. 1 illustrates an expanded and cross-sectional view of a flow cell 100 and illustrates a portion of a flow chamber 106. A reagent flow 108 flows across a surface of a microwell array 102, in which the reagent flow 108 flows over the open ends of microwells of the microwell array 102. The microwell array 102 and a sensor array 105 together may form an integrated unit forming a lower wall (or floor) of flow cell 100. A reference electrode 104 may be fluidly coupled to flow chamber 106. Further, a flow cell cover 130 encapsulates flow chamber 106 to contain reagent flow 108 within a confined region.

Figure 2:
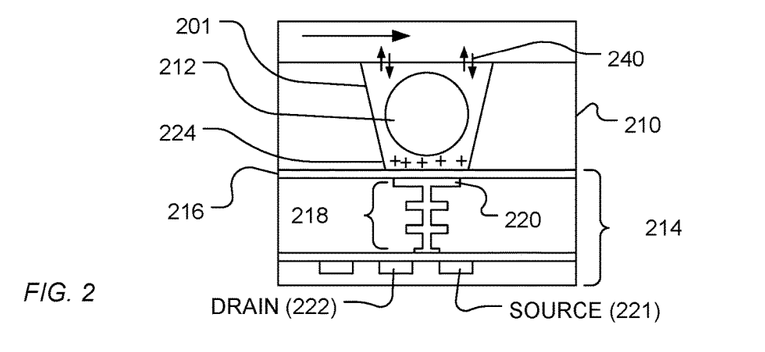
FIG. 2 includes an illustration of an exemplary sensor and associated well.

FIG. 2 illustrates an expanded view of a microwell 201 and a sensor 214, as illustrated at 110 of FIG. 1. The volume, shape, aspect ratio (such as base width-to-well depth ratio), and other dimensional characteristics of the microwells may be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 optionally separated from the microwell interior by a passivation layer 216. The sensor 214 can be responsive to (and generate an output signal related to) the amount of a charge 224 present on passivation layer 216 opposite the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, wash solutions, and other reagents may move in and out of the microwells by a diffusion mechanism 240.

In an embodiment, reactions carried out in the microwell 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, then multiple copies of the same analyte may be analyzed in the microwell 201 at the same time in order to increase the output signal generated. In an embodiment, multiple copies of an analyte may be attached to a solid phase support 212, either before or after deposition into the microwell 201. The solid phase support 212 may be microparticles, nanoparticles, beads, solid or porous comprising gels, or the like. For simplicity and ease of explanation, solid phase support 212 is also referred herein as a particle. For a nucleic acid analyte, multiple, connected copies may be made by rolling circle amplification (RCA), exponential RCA, or like techniques, to produce an amplicon without the need of a solid support.

In particular, the solid phase support can include copies of polynucleotides. In a particular example illustrated in FIG. 3, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

In general, the polymeric particle can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

Figure 3:
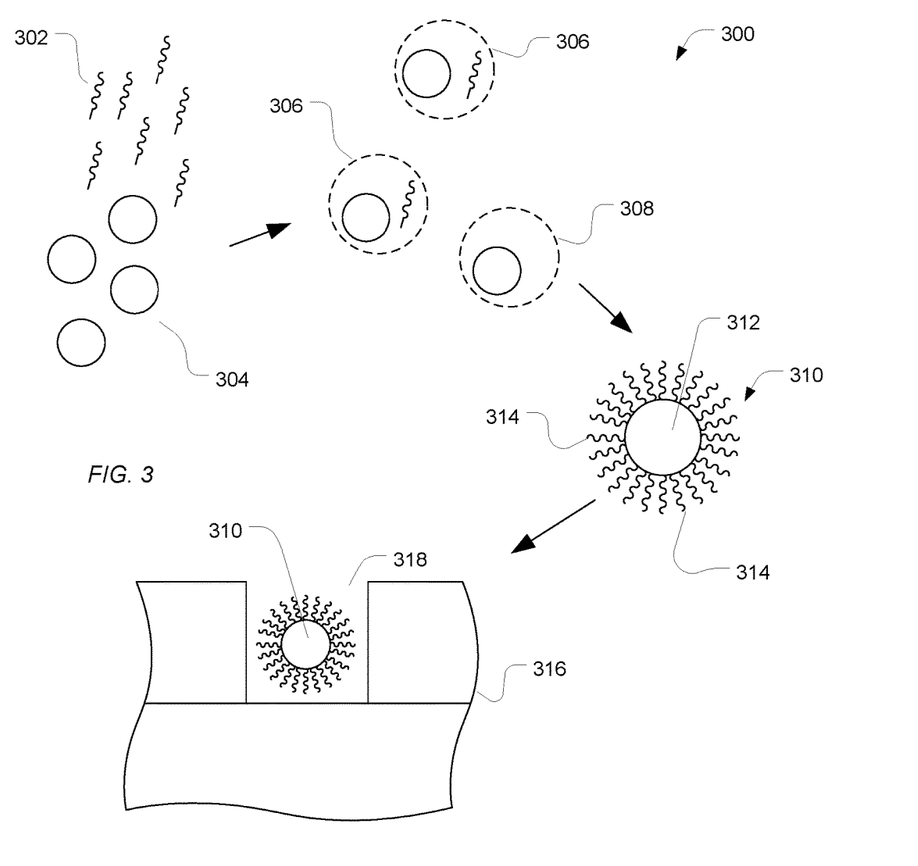
FIG. 3 includes an illustration of exemplary methods for preparing a sequencing device.

As illustrated in FIG. 3, a plurality of polymeric particles 304 can be placed in a solution along with a plurality of polynucleotides 302. The plurality of particles 304 can be activated or otherwise prepared to bind with the polynucleotides 302. For example, the particles 304 can include an oligonucleotide complementary to a portion of a polynucleotide of the plurality of polynucleotides 302. In another example, the polymeric particles 304 can be modified with target polynucleotides 304 using techniques such as biotin-streptavidin binding.

In a particular embodiment, the hydrophilic particles and polynucleotides are subjected to polymerase chain reaction (PCR) amplification or recombinase polymerase amplification (RPA). For example, dispersed phase droplets 306 or 308 are formed as part of an emulsion and can include a hydrophilic particle or a polynucleotide. In an example, the polynucleotides 302 and the hydrophilic particles 304 are provided in low concentrations and ratios relative to each other such that a single polynucleotide 302 is likely to reside within the same dispersed phase droplets as a single hydrophilic particle 304. Other droplets, such as a droplet 308, can include a single hydrophilic particle and no polynucleotide. Each droplet 306 or 308 can include enzymes, nucleotides, salts or other components sufficient to facilitate duplication of the polynucleotide.

In a particular embodiment, an enzyme such as a polymerase is present, bound to, or is in close proximity to the hydrophilic particle or hydrogel particle of the dispersed phase droplet. In an example, a polymerase is present in the dispersed phase droplet to facilitate duplication of the polynucleotide. A variety of nucleic acid polymerase may be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

Following PCR or RPA, particles are formed, such as particle 310, which can include the hydrophilic particle 312 and a plurality of copies 314 of the polynucleotide. While the polynucleotides 314 are illustrated as being on a surface of the particle 310, the polynucleotides can extend within the particle 310. Hydrogel and hydrophilic particles having a low concentration of polymer relative to water can include polynucleotide segments on the interior of and throughout the particle 310 or polynucleotides can reside in pores and other openings. In particular, the particle 310 can permit diffusion of enzymes, nucleotides, primers and reaction products used to monitor the reaction. A high number of polynucleotides per particle produces a better signal.

In embodiments, polymeric particles from an emulsion-breaking procedure can be collected and washed in preparation for sequencing. Collection can be conducted by contacting biotin moieties (e.g., linked to amplified polynucleotide templates which are attached to the polymeric particles) with avidin moieties, and separation away from polymeric particles lacking biotinylated templates. Collected polymeric particles that carry double-stranded template polynucleotides can be denatured to yield single-stranded template polynucleotides for sequencing. Denaturation steps can include treatment with base (e.g., NaOH), formamide, or pyrrolidone.

In an exemplary embodiment, the particle 310 can be utilized in a sequencing device. For example, a sequencing device 316 can include an array of wells 318. The sequencing device 316 can be treated with a wash solution including sulfonic acid, as described above. A particle 310 can be placed within a well 318.

In an example, a primer can be added to the wells 318 or the particle 310 can be pre-exposed to the primer prior to placement in the well 318. In particular, the particle 310 can include bound primer. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 318 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 316 and can migrate to the well 318. Excitation energy can be also provided to the well 318. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 318 can change. Such a change in pH can be detected by ion sensitive field effect transistors (ISFET). As such, a change in pH can be used to generate a signal indicating the order of nucleotides complementary to the polynucleotide of the particle 310.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In embodiments, one or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 3, in another example, a well 318 of the array of wells can be operatively connected to measuring devices. For example, for fluorescent emission methods, a well 318 can be operatively coupled to a light detection device. In the case of ionic detection, the lower surface of the well 318 may be disposed over a sensor pad of an ionic sensor, such as a field effect transistor.

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

Figure 4:
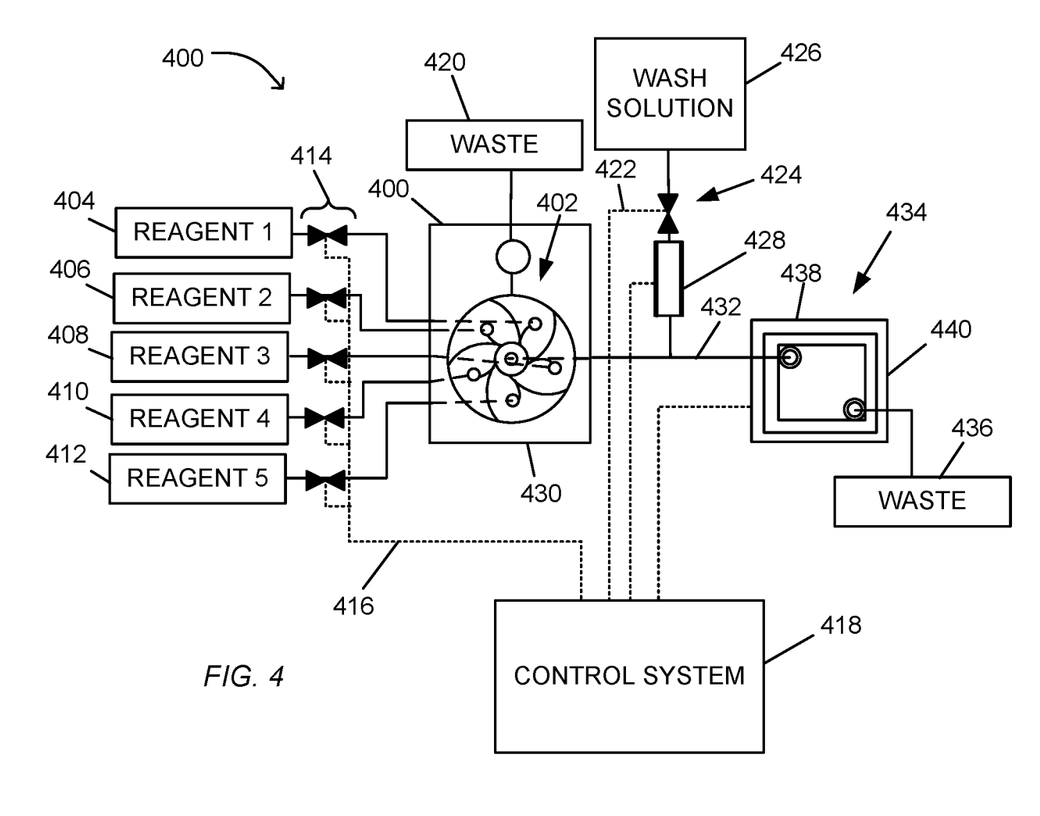
FIG. 4 is a block diagram describing an example system.

FIG. 4 diagrammatically illustrates a system employing a valve, for example, for carrying out pH-based nucleic acid sequencing. Each electronic sensor of the apparatus generates an output signal that depends on the value of a reference voltage. The fluid circuit permits multiple reagents to be delivered to the reaction chambers.

In FIG. 4, system 400 containing fluidics circuit 402 is connected by inlets to at least two reagent reservoirs (404, 406, 408, 410, or 412), to waste reservoir 420, and to biosensor 434 by fluid pathway 432 that connects fluidics node 430 to inlet 438 of biosensor 434 for fluidic communication. Reagents from reservoirs (404, 406, 408, 410, or 412) can be driven to fluidic circuit 402 by a variety of methods including pressure, pumps, such as syringe pumps, gravity feed, and the like, and are selected by control of valves 414. Reagents from the fluidics circuit 402 can be driven through the valves 414 receiving signals from control system 418 to waste container 420. Reagents from the fluidics circuit 402 can also be driven through the biosensor 434 to the waste container 436. The control system 418 includes controllers for valves, which generate signals for opening and closing via electrical connection 416.

The control system 418 also includes controllers for other components of the system, such as wash solution valve 424 connected thereto by electrical connection 422, and reference electrode 428. Control system 418 can also include control and data acquisition functions for biosensor 434. In one mode of operation, fluidic circuit 402 delivers a sequence of selected reagents 1, 2, 3, 4, or 5 to biosensor 434 under programmed control of control system 418, such that in between selected reagent flows, fluidics circuit 402 is primed and washed, and biosensor 434 is washed. Fluids entering biosensor 434 exit through outlet 440 and are deposited in waste container 436 via control of pinch valve regulator 444. The valve 444 is in fluidic communication with the sensor fluid output 440 of the biosensor 434.

Figure 5:
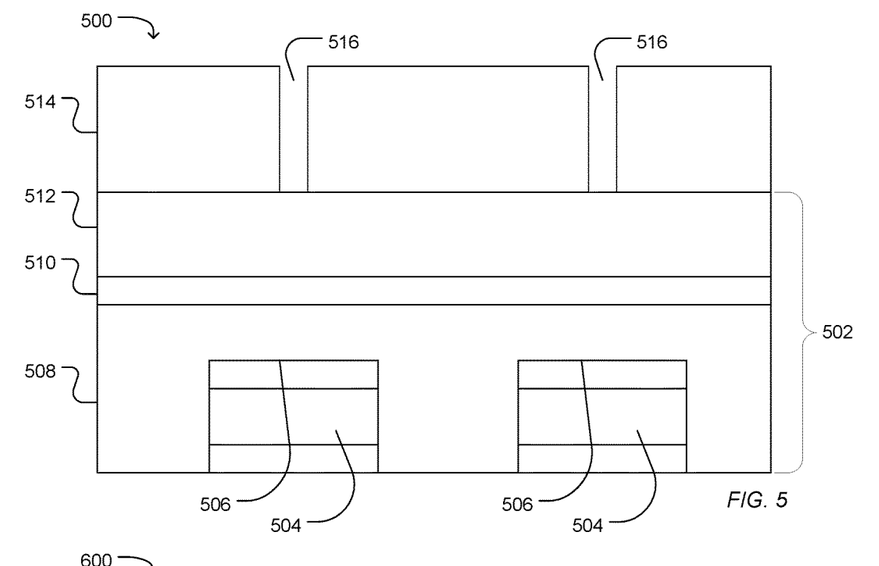
FIG. 5, FIG. 6, FIG. 7, FIG. 8, FIG. 9, FIG. 10, and FIG. 11 include illustrations of example work pieces during a process for making a microwell.

FIG. 5, FIG. 6, FIG. 7, FIG. 8, FIG. 9, FIG. 10, and FIG. 11 illustrate work pieces during a process for forming a microwell. For example, as illustrated in FIG. 5, a work piece 500 includes dielectric structure 502 deposited over and surrounding a sensor pad 504 having a sensing surface 506. The dielectric structure 502 can have more than one layer. For example, the illustrated dielectric structure 502 includes a high density plasma chemical vapor deposited silicon dioxide layer 508, a silicon nitride layer 510 deposited over the silicon oxide layer 508, and a TEOS silicon oxide layer 512 deposited over the silicon nitride layer 510. Alternatively, the dielectric structure can be formed of a single silicon oxide layer, a single silicon nitride layer, or one silicon oxide layer and one silicon nitride layer. A photoresist layer 514 can disposed over the dielectric structure 502 and can be patterned to defined photoresist openings 516 positioned over the sensor pads 504.

Figure 6:
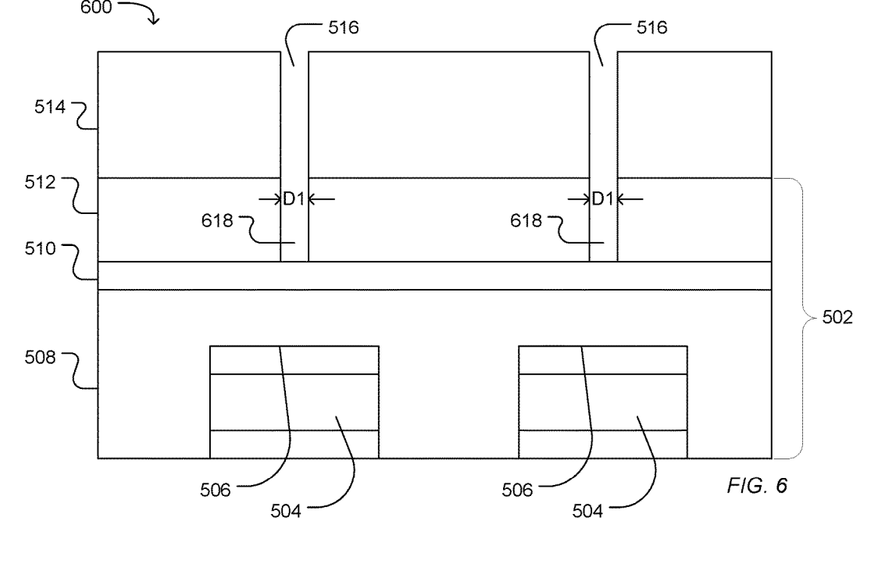

The work piece can be etched to form a first access at least partially through the dielectric structure 502 above the sensor pads 504. For example, as illustrated in FIG. 6, a work piece 600 is etched to define a first access 618 at least partially through the dielectric structure 502. In the illustrated example, the first access 618 extends through a silicon oxide layer 512. Alternatively, the first access 618 can extend into the silicon nitride layer 510 or at least partially into a high density plasma chemical vapor deposited silicon dioxide layer 508. As illustrated the first access 618 does not extend through the dielectric structure to the sensor pad surface 506. Alternatively, the first access 618 can be etched to contact the surface 506 of the sensor pad 504.

Etching can be implemented by a wet etch or a plasma etch. In an example, etching includes plasma etching in chemistries selective to the layer being etched.

The first access 618 can have a characteristic diameter. In an example, the characteristic diameter of the first access 618 can be in a range of 0.05 µm to 0.5 µm, such as a range of 0.1 µm to 0.4 µm or a range of 0.20 µm to 0.35 µm.

Figure 7:
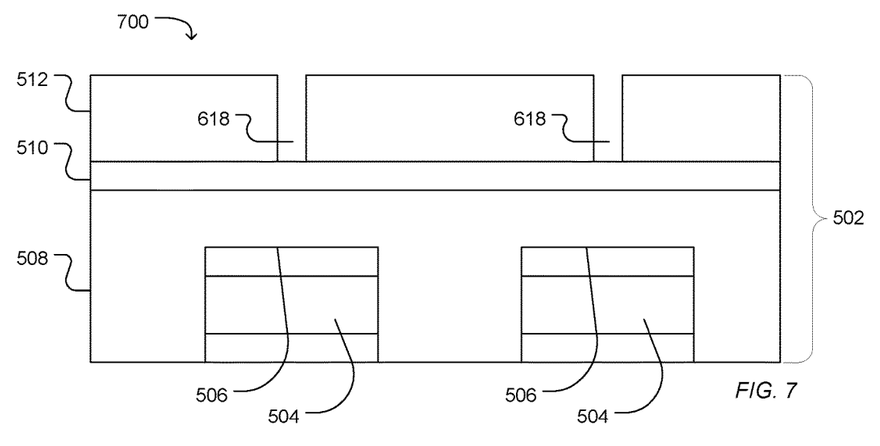
Figure 8:
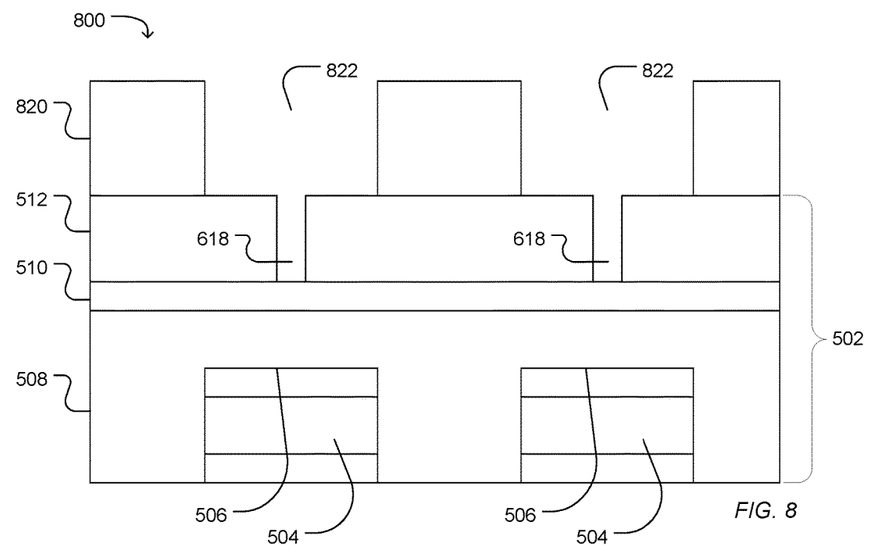

FIG. 7 illustrates the work piece 700 following aching and cleaning the photoresist layer 514, for example, with an oxygen rich plasma or solvent. As illustrated in FIG. 8, a work piece 800 includes a photoresist layer 820 pattern with a photoresist opening 822. The opening 822 is disposed over the first access 618 and over the sensor pad 504 and at least partially overlaps the first access 618 and the sensor pad 504 when observed from a top view. In a particular example, the opening 822 is concentric with an axis of the first access 618.

Figure 9:
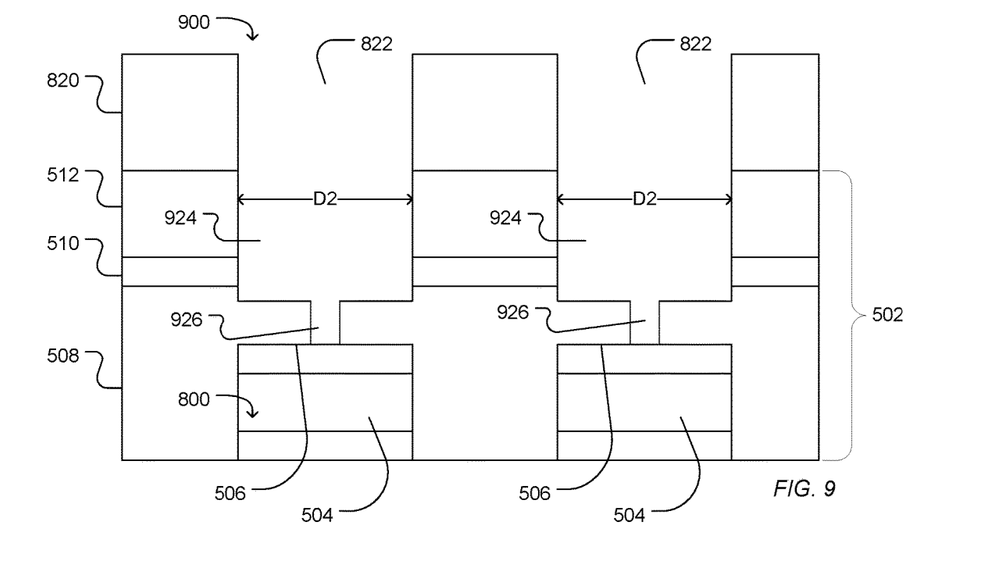

A second access can be etched into the work piece 800 resulting in a work piece 900 illustrated in FIG. 9. In an example in which the first access 618 does not extend through to the dielectric structure 502 to expose the sensor pad 504 following the first etching process, the first access 618 can be extended to contact the surface 506 of the sensor pad 504 forming an extended first access 926 between the second access 924 and the sensor pad surface 506. In the illustrated example, the second access 924 extends through the dielectric structure 502 but does not reach the sensor pad surface 506. For example, the second access 924 can extend through the low temperature silicon oxide layer 512, optionally through a silicon nitride layer 510, and may extend partially into a high density silicon oxide layer 508.

The second access 924 can have a characteristic diameter in a range of 0.4 µm to 3.0 µm, such as a range of 0.4 µm to 2.1 µm, a range of 0.4 µm to 1.6 µm, a range of 0.5 µm to 1.1 µm, or a range of 0.6 µm to 0.8 µm. In particular, a diameter ratio between the characteristic diameter of the first access and the characteristic diameter of the second access can be in a range of 0.01 to 0.7. For example, the diameter ratio defined as the ratio of the characteristic diameter of the first access to the characteristic diameter of the second access can be in a range of 0.05 to 0.6, such as a range of 0.1 to 0.6, or a range of 0.3 to 0.6.

Figure 10:
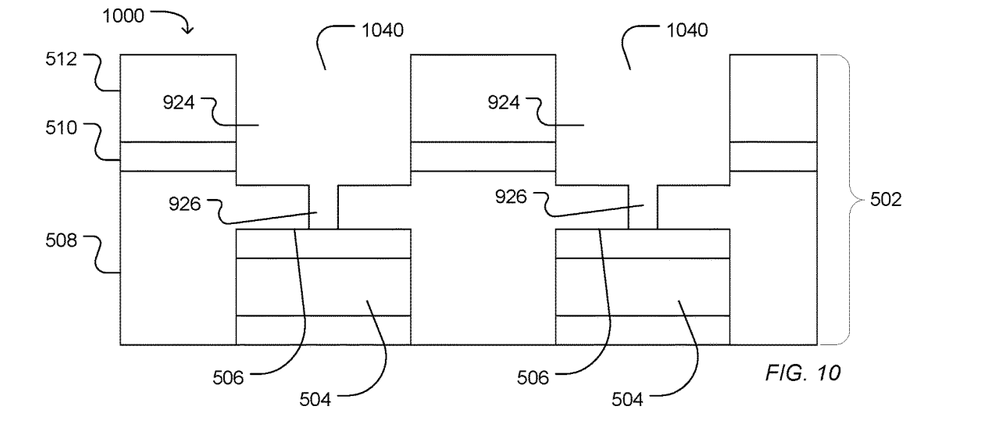

FIG. 10 illustrates a work piece 1000 following aching and cleaning of the photoresist layer 820. For example, the work piece can be subjected to an oxygen plasma treatment, followed by a vapor hydrogen fluoride treatment and cleaning with a solvent, such as N-methyl pyrrolidone (NMP). As illustrated, the extended first access 926 and the second access 924 form a microwell 1040.

Figure 11:
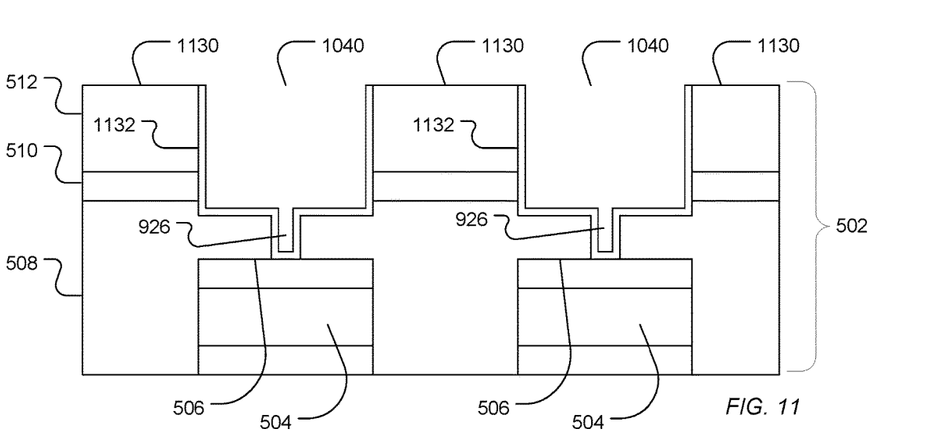

Optionally, as illustrated in FIG. 11, a conformal metal layer 1132 can be deposited into the microwell 1040 formed from the first access 926 and the second access 924. For example, a metal, such as titanium, tungsten, gold, silver, tantalum, zirconium, aluminum, copper, hafnium, or a combination thereof, can be sputtered, deposited, or a combination thereof to form a conformal coating 1132 over the surface of the microwell 1040. The conformal metal coating 1132 can be removed from interstitial areas 1130. For example, the wells 1040 can be filled with polyimide followed by chemical mechanical polishing of both polyimide and metal from the interstitial spaces 1130. The polyimide can optionally be removed by solvent, an oxygen plasma process, an additional solvent bath, or a combination thereof.

Figure 12:
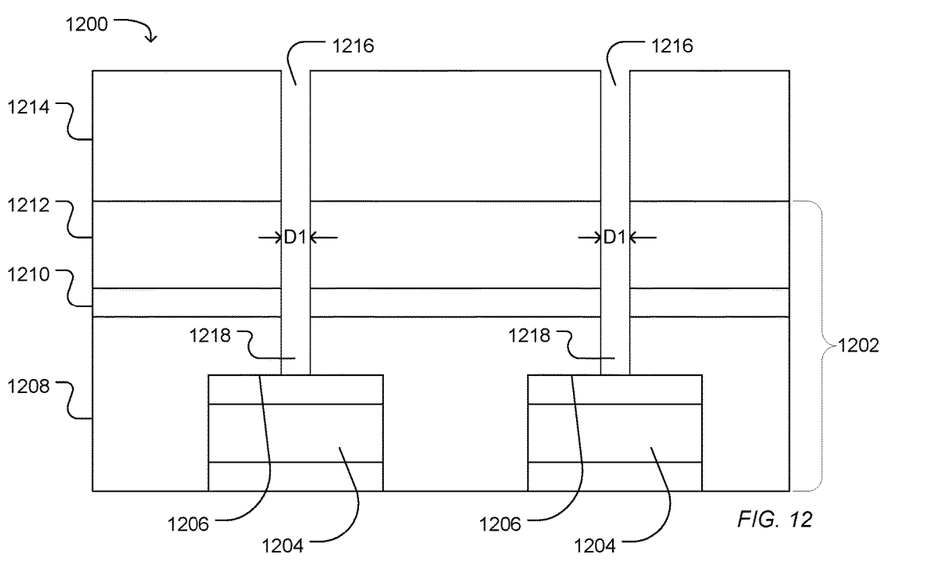
FIG. 12, FIG. 13, FIG. 14, FIG. 15, FIG. 16, FIG. 17, and FIG. 18 include illustrations of example steps in a process for forming a microwell.

In another example illustrated in FIG. 12, a work piece 1200 includes a dielectric structure 1202 deposited over sensor pads 1204 having sensor surfaces 1206. The dielectric structure 1202 can be formed of one or more layers. In the illustrated example, the dielectric structure 1202 includes a high density plasma chemical vapor deposited silicon dioxide layer 1208, a silicon nitride layer 1210 deposited over the silicon oxide layer 1208, and a silicon oxide layer 1212 deposited over the silicon nitride layer 1210. A photoresist layer 1214 can be formed and patterned to define photoresist openings 1216. The dielectric structure 1202 can then be etched to form a first access 1218 that extends through the dielectric structure 1202 to expose the sensor surface 1206. The first access 1218 can have the characteristic diameter described above in relation to the first access 618. Etching can include a wet etch or a plasma etch. In particular, etching includes a plasma etch.

Figure 13:
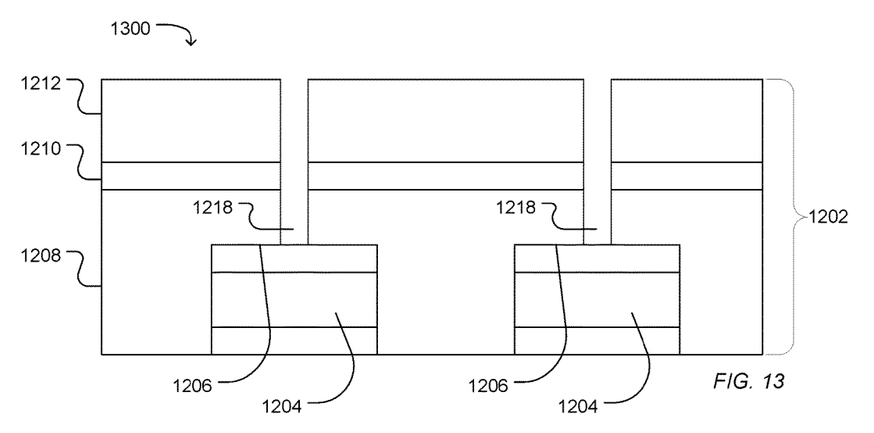

As illustrated in FIG. 13, the photoresist layer 1214 can be cleaned from the surface, leaving the dielectric structure 1202 defining first access 1218 exposing the sensor pad surface 1206.

Figure 14:
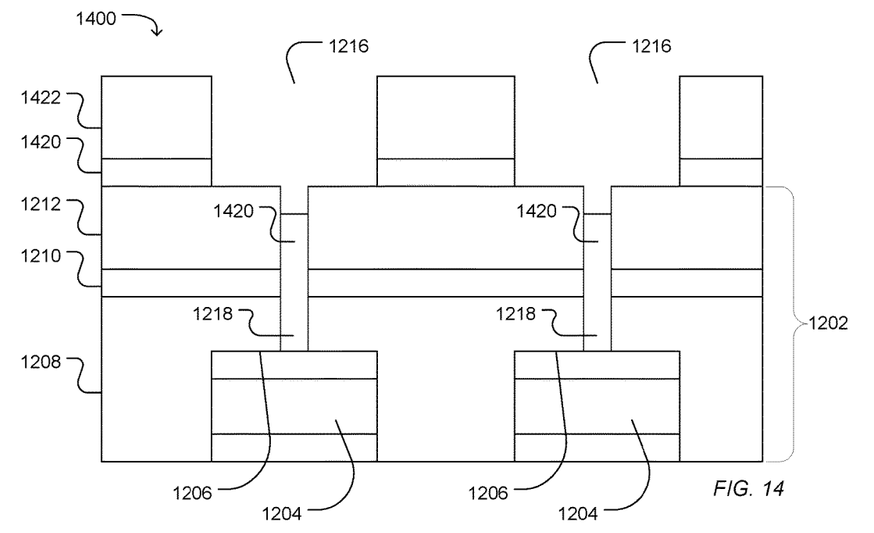

As illustrated in FIG. 14, a bottom anti-reflective coating (BARC) 1420 can be formed over the dielectric structure 1202, and a photoresist layer 1422 can be formed over the bottom anti-reflective coating (BARC) layer 1420. The photoresist layer 1422 and optionally the BARC layer 1420 can be patterned to define photoresist openings 1424. The BARC layer 1420 at least partially deposits into the first access 1218. The photoresist openings 1424 can overlap the first access 1218 and the sensor pad 1204 from a top view. In particular, the photoresist opening 1424 can be concentric with an axis of the first access 1218.

Figure 15:
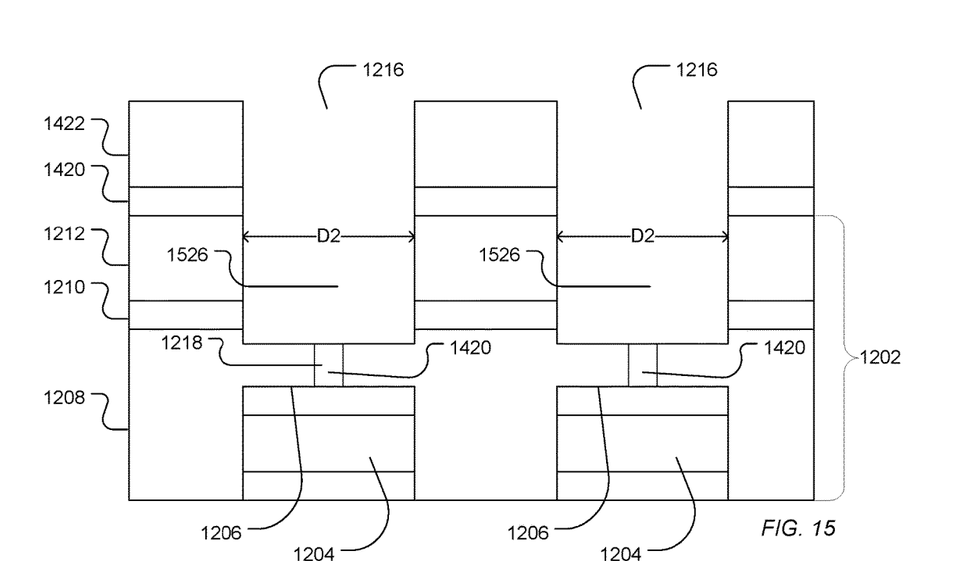

As illustrated in FIG. 15, a second access 1526 can be etched into the dielectric structure 1202. For example, the second access 1526 can be etched using a plasma etch. At least a portion of the BARC layer 1420 remains in the first access 1218, potentially protecting the sensor pad surface 1206 from exposure to the plasma etching of the second access 1526.

The second access 1526 can have a characteristic diameter similar to the characteristic diameter described above in relation to the second access 924 described above. Further, the diameter ratio of the characteristic diameter of the first access 1218 to the characteristic diameter of the second access 1526 can have can have the diameter ratio described above in relation to the first access 618 and the second access 924 described above.

Figure 16:
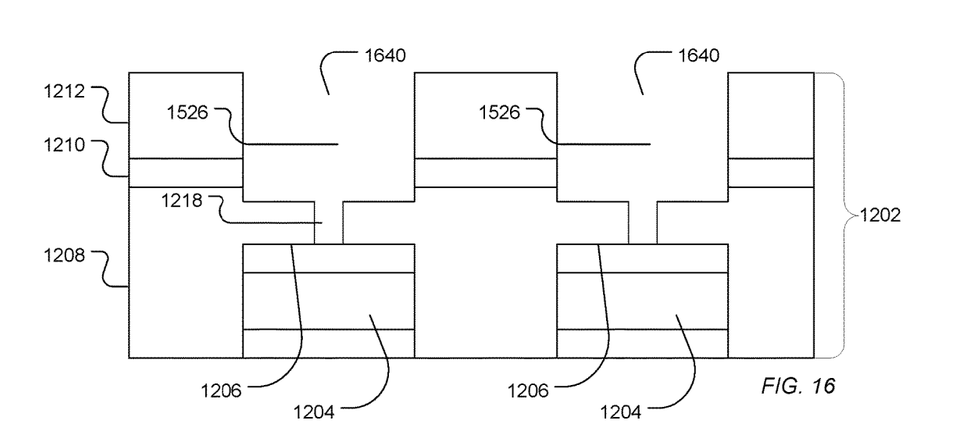

As illustrated in FIG. 16, the photoresist layer 1422 and the BARC layer 1420 can be cleaned from the surface. For example, the layers can be cleaned using an oxygen plasma, a vapor hydrogen fluoride treatment, an NMP solvent, or a combination thereof. The first access 1218 and the second access 1526 form a well 1640.

Figure 17:
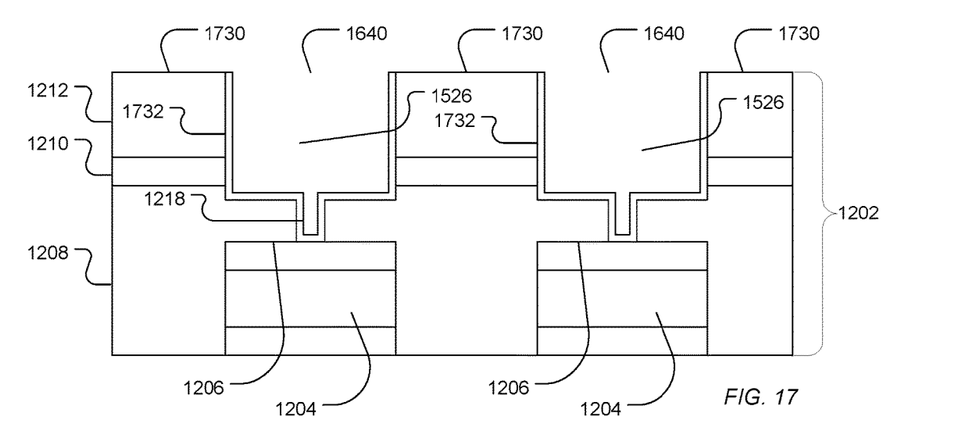

In a further example illustrated in FIG. 17, a conformal metal coating 1732 can be deposited into the wells 1640 formed by the first access 1218 and the second access 1526. For example, a metal layer can be deposited using sputtering or a vapor deposition or a combination thereof followed by providing a protective polymer coating and performing chemical mechanical polishing to remove the metal layer from interstitial areas 1730.

The polymer coating can be removed using solvent treatments, plasma ashing methods or a combination thereof. In an alternative example illustrated in FIG. 18, the polymer coating can remain in place in the wells while an additional dielectric structure 1834 is deposited over the dielectric structure 1202. For example, an additional oxide layer 1834 can be deposited over the dielectric layer 1202 using plasma enhanced chemical vapor deposition (PECVD). Photoresist can be formed over the oxide layer 1834 and the photoresist layer can be patterned to define further openings overlapping with the first access and the second access. An additional access can be etched through the oxide layer 1832 to provide a third access 1836 in fluid communication with the second accesses 1526. The protective polymer in the second access 1526 and the first access 1218 can be removed along with the photoresist layer using solvent sprays, oxygen plasma ashing, an NMP bath, or a combination thereof. While the formation of the additional oxide layer 1832 is described in relation to the process illustrated in FIGS. 12 through 17, such a layer can also be formed following the process illustrated in FIGS. 5 through 11.

Figure 18:
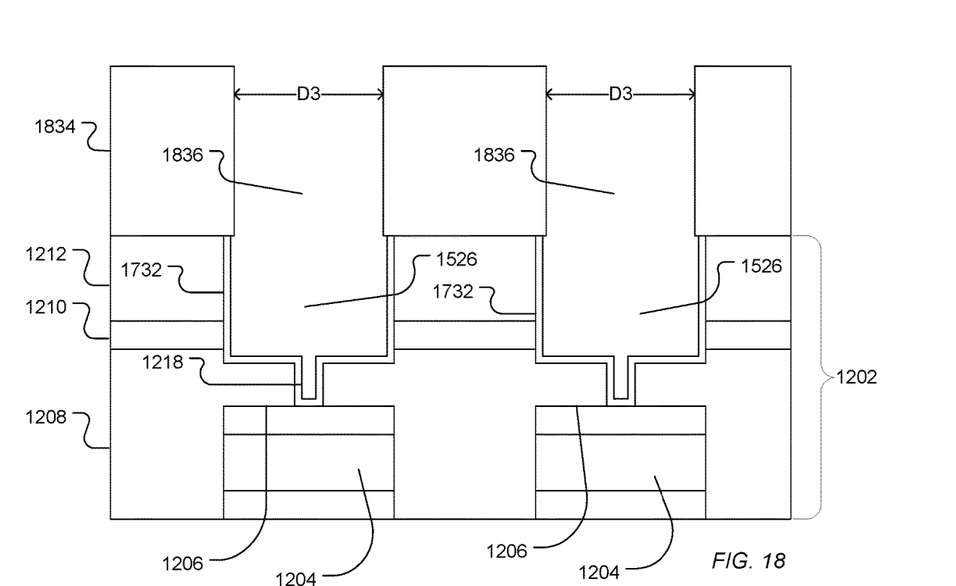

The characteristic diameter of the third access 1836 can be in a range of 0.4 µm to 3 µm, such as a range of 0.4 µm to 2.1 µm, a range of 0.4 µm to 1.6 µm, a range of 0.5 µm to 1.1 µm, or a range of 0.6 µm to 0.8 µm. The characteristic diameter of the third access 1836 can be similar to the characteristic diameter of the second access 1526. In another example, the characteristic diameter of the third access 1836 can be smaller than the characteristic diameter of the second access 1526.

The above described methods yield desirable technical advantages. The etch chemistry can be selected to etch silicon oxides and nitrides while minimally affecting photoresist. Further, etching the second access proceeds to the desired depth of the well and not to the depth of the sensor surface. The photoresist can better tolerate such an etch process. In addition, when using a BARC layer, the sensor pad is not exposed during the second etch process.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for forming a well providing access to a sensor pad, the method comprising:
   patterning a first photoresist layer over a dielectric structure disposed over the sensor pad;
   etching a first access into the dielectric structure and over the sensor pad, the first access having a first characteristic diameter;
   depositing a bottom anti-reflective coating following etching the first access, wherein the bottom anti-reflective coating is at least partially disposed in the first access;
   patterning a second photoresist layer over the dielectric structure after depositing a bottom anti-reflective coating; and
   etching a second access over the dielectric structure and over the sensor pad, the second access having a second characteristic diameter, the first and second accesses overlapping, a diameter ratio of the first characteristic diameter to the second characteristic diameter being not greater than 0.7, the first access exposing the sensor pad, the second access having a bottom depth less than a bottom depth of the first access.

2. The method of claim 1, wherein the diameter ratio is in a range of 0.01 to 0.7.

3. The method of claim 2, wherein the diameter ratio is in a range of 0.05 to 0.6.

4. The method of claim 3, wherein the diameter ratio is in a range of 0.1 to 0.6.

5. The method of claim 4, wherein the diameter ratio is in a range of 0.3 to 0.6.

6. The method of claim 1, wherein etching the first access includes etching the first access to a bottom depth to expose the sensor pad.

7. The method of claim 1, wherein etching the first access includes etching the first access to a bottom depth that does not expose the sensor pad.

8. The method of claim 1, wherein the dielectric structure includes an oxide layer and a nitride layer.

9. The method of claim 8, wherein the oxide layer is a high density plasma chemical vapor deposited silicon dioxide layer.

10. The method of claim 8, wherein the dielectric structure further includes a tetraethyl orthosilicate deposited oxide layer.

11. The method of claim 10, wherein etching the first access includes etching the first access through the low temperature oxide layer, the nitride layer and the oxide layer.

12. The method of claim 10, wherein etching the first access includes etching the first access through the low temperature oxide layer and not the oxide layer.

13. The method of claim 10, wherein etching the second access includes etching the second access through the low temperature oxide layer and the nitride layer.

14. The method of claim 13, wherein etching the second access includes etching the second access partially into the oxide layer.

15. The method of claim 1, further comprising cleaning with an oxygen ash step following etching the second access.

16. The method of claim 15, further comprising performing a vapor hydrogen fluoride treatment following the oxygen ash step.

17. The method of claim 1, further comprising depositing a conformal metal coating over the first and second accesses following etching the second access.

18. The method of claim 17, further comprising removing the conformal metal coating from interstitial areas over the dielectric structure.

* * * * *